(12) United States Patent
Single

(10) Patent No.: US 12,369,826 B2
(45) Date of Patent: *Jul. 29, 2025

(54) NEURAL MEASUREMENT

(71) Applicant: Saluda Medical Pty Ltd, Artarmon (AU)

(72) Inventor: Peter Scott Vallack Single, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 368 days.

This patent is subject to a terminal disclaimer.

(21) Appl. No.: 17/815,661

(22) Filed: Jul. 28, 2022

(65) Prior Publication Data
US 2023/0021564 A1    Jan. 26, 2023

Related U.S. Application Data

(63) Continuation of application No. 16/532,364, filed on Aug. 5, 2019, now Pat. No. 11,457,849, which is a
(Continued)

(30) Foreign Application Priority Data

May 5, 2014    (AU) .................................. 2014901639

(51) Int. Cl.
*A61B 5/00* (2006.01)
*A61B 5/24* (2021.01)
(Continued)

(52) U.S. Cl.
CPC .................. *A61B 5/24* (2021.01); *A61B 5/30* (2021.01); *A61B 5/311* (2021.01); *A61B 5/7203* (2013.01);
(Continued)

(58) Field of Classification Search
CPC .. A61B 5/24; A61B 5/311; A61B 5/30; A61B 5/7203; A61N 1/0541;
(Continued)

(56) References Cited

U.S. PATENT DOCUMENTS 3,724,467 A    4/1973 Avery et al.
3,736,434 A    5/1973 Darrow
(Continued)

FOREIGN PATENT DOCUMENTS

AU    2013277009    1/2016
CN    103648583    3/2014
(Continued)

OTHER PUBLICATIONS

"Advanced Pain Therapy using Neurostimulation for Chronic Pain", Medtronic RestoreSensor clinical trial paper, Clinical summary, Nov. 2011, pp. 32.
(Continued)

*Primary Examiner* — Eugene T Wu
(74) *Attorney, Agent, or Firm* — Barnes & Thornburg LLP

(57) ABSTRACT

Measuring a neural response to a stimulus comprises applying an electrical stimulus, then imposing a delay during which the stimulus electrodes are open circuited. During the delay, a neural response signal present at sense electrodes is measured with a measurement amplifier, while ensuring that an impedance between the sense electrodes is sufficiently large that a voltage arising on the sense electrode tissue interface in response to the stimulus is constrained to a level which permits assessment of the neural response voltage seen at the sense electrode. For example the input impedance to the measurement amplifier (ZIN) can be, where ZC is the sense electrode(s) constant phase element impedance, Vs1–Vs2 is the differential voltage arising on the sense electrode
(Continued)

tissue interface, and VE is the neural response voltage seen at the sense electrode.

34 Claims, 6 Drawing Sheets

Related U.S. Application Data continuation of application No. 15/307,770, filed as application No. PCT/AU2015/050215 on May 5, 2015, now Pat. No. 10,368,762.

(51) Int. Cl.
- *A61B 5/30* (2021.01)
- *A61B 5/311* (2021.01)
- *A61N 1/05* (2006.01)
- *A61N 1/36* (2006.01)

(52) U.S. Cl.
CPC ......... *A61N 1/0529* (2013.01); *A61N 1/0541* (2013.01); *A61N 1/0551* (2013.01); *A61N 1/36125* (2013.01); *A61N 1/36128* (2013.01); *A61N 1/36135* (2013.01)

(58) Field of Classification Search
CPC .............. A61N 1/36135; A61N 1/0529; A61N 1/0551; A61N 1/36128
See application file for complete search history.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King et al. |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van Oort |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,538,541 B2 | 9/2013 | Milojevic et al. |
| 8,588,929 B2 | 11/2013 | Davis et al. |
| 8,620,459 B2 | 12/2013 | Gibson et al. |
| 8,655,002 B2 | 2/2014 | Parker |
| 8,670,830 B2 | 3/2014 | Carlson et al. |
| 8,886,323 B2 | 11/2014 | Wu et al. |
| 8,945,216 B2 | 2/2015 | Parker et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,566,439 B2 | 2/2017 | Single et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,457,849 B2 | 10/2022 | Single |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |

(56) References Cited

U.S. PATENT DOCUMENTS

| | | |
|---|---|---|
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Bradley et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0033486 A1 | 2/2009 | Costantino et al. |
| 2009/0058635 A1 | 3/2009 | Parker |
| 2009/0082691 A1 | 3/2009 | Denison et al. |
| 2009/0149912 A1 | 6/2009 | Dacey et al. |
| 2009/0157155 A1 | 6/2009 | Bradley |
| 2009/0270957 A1 | 10/2009 | Pianca |
| 2009/0281594 A1 | 11/2009 | King et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson et al. |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Tamir et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Bennett et al. |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Aritome |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0268043 A1 | 10/2013 | Tasche et al. |
| 2013/0289661 A1 | 10/2013 | Griffith et al. |
| 2013/0289683 A1 | 10/2013 | Parker et al. |
| 2014/0046407 A1 | 2/2014 | Ben-Ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0051637 A1 | 2/2015 | Osorio |
| 2015/0126839 A1 | 5/2015 | Li et al. |

(56) References Cited

U.S. PATENT DOCUMENTS

| | | |
|---|---|---|
| 2015/0148869 A1 | 5/2015 | Dorvall et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Surth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0256068 A1* | 9/2016 | Harrison ............... A61B 5/053 |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0016091 A1 | 1/2021 | Parker et al. |
| 2021/0121696 A1 | 4/2021 | Parker et al. |
| 2021/0162214 A1 | 6/2021 | Parker |

FOREIGN PATENT DOCUMENTS

| | | |
|---|---|---|
| CN | 103654762 | 3/2014 |
| CN | 103842022 | 6/2014 |
| CN | 104411360 | 3/2015 |
| EP | 0219084 | 4/1987 |
| EP | 1244496 | 10/2002 |
| EP | 0998958 | 8/2005 |
| EP | 2019716 | 11/2007 |
| EP | 2243510 | 10/2010 |
| EP | 2443995 | 4/2012 |
| EP | 2520327 | 11/2012 |
| EP | 2707095 | 3/2014 |
| EP | 3229893 | 10/2017 |
| JP | 2006504494 | 2/2006 |
| JP | 2009512505 | 3/2009 |
| JP | 2012524629 | 10/2012 |
| JP | 2013500779 | 1/2013 |
| JP | 2013527784 | 7/2013 |
| JP | 2013536044 | 9/2013 |
| JP | 2014522261 | 9/2014 |
| JP | 2014523261 | 9/2014 |
| WO | WO 1983003191 | 9/1983 |
| WO | WO 1993001863 | 2/1993 |
| WO | WO 1996012383 | 4/1996 |
| WO | WO 2000002623 | 1/2000 |
| WO | WO 2002036003 | 11/2001 |
| WO | WO 2002038031 | 5/2002 |
| WO | WO 2002049500 | 6/2002 |
| WO | WO 2003028521 | 4/2003 |
| WO | WO 2003043690 | 5/2003 |
| WO | WO 2003103484 | 12/2003 |
| WO | WO 2004021885 | 3/2004 |
| WO | WO 2004103455 | 12/2004 |
| WO | WO 2005032656 | 4/2005 |
| WO | WO 2005105202 | 11/2005 |
| WO | WO 2005122887 | 12/2005 |
| WO | WO 2006091636 | 8/2006 |
| WO | WO 2007050657 | 5/2007 |
| WO | WO 2007064936 | 6/2007 |
| WO | WO 2007127926 | 11/2007 |
| WO | WO 2007130170 | 11/2007 |
| WO | WO 2008004204 | 1/2008 |
| WO | WO 2008049199 | 5/2008 |
| WO | WO 2009002072 | 12/2008 |
| WO | WO 2009002579 | 12/2008 |
| WO | WO 2009010870 | 1/2009 |
| WO | WO 2009130515 | 10/2009 |
| WO | WO 2009146427 | 12/2009 |
| WO | WO 2010013170 | 2/2010 |
| WO | WO 2010044989 | 4/2010 |
| WO | WO 2010051392 | 5/2010 |
| WO | WO 2010051406 | 5/2010 |
| WO | WO 2010057046 | 5/2010 |
| WO | WO 2010124139 | 10/2010 |
| WO | WO 2010138915 | 12/2010 |
| WO | WO 2011011327 | 1/2011 |
| WO | WO 2011014570 | 2/2011 |
| WO | WO 2011017778 | 2/2011 |
| WO | WO 2011066477 | 6/2011 |
| WO | WO 2011066478 | 6/2011 |
| WO | WO 2011112843 | 9/2011 |
| WO | WO 2011119251 | 9/2011 |
| WO | WO 2011159545 | 12/2011 |
| WO | WO 2012027252 | 3/2012 |
| WO | WO 2012027791 | 3/2012 |
| WO | WO 2012155183 | 11/2012 |
| WO | WO 2012155184 | 11/2012 |
| WO | WO 2012155185 | 11/2012 |
| WO | WO 2012155187 | 11/2012 |
| WO | WO 2012155188 | 11/2012 |
| WO | WO 2012155189 | 11/2012 |
| WO | WO 2012155190 | 11/2012 |
| WO | WO 2012162349 | 11/2012 |
| WO | WO 2013063111 | 5/2013 |
| WO | WO 2013075171 | 5/2013 |
| WO | WO 2014071445 | 5/2014 |
| WO | WO 2014071446 | 5/2014 |
| WO | WO 2014143577 | 9/2014 |
| WO | WO 2014150001 | 9/2014 |
| WO | WO 2015070281 | 5/2015 |
| WO | WO 2015074121 | 5/2015 |
| WO | WO 2015109239 | 7/2015 |
| WO | WO 2015143509 | 10/2015 |
| WO | WO 2015168735 | 11/2015 |
| WO | WO 2016011512 | 1/2016 |
| WO | WO 2016048974 | 3/2016 |
| WO | WO 2016059556 | 4/2016 |
| WO | WO 2016077882 | 5/2016 |
| WO | WO 2016090420 | 6/2016 |
| WO | WO 2016090436 | 6/2016 |
| WO | WO 2016115596 | 7/2016 |
| WO | WO 2016161484 | 10/2016 |
| WO | WO 2016168798 | 10/2016 |
| WO | WO 2016191807 | 12/2016 |
| WO | WO 2016191808 | 12/2016 |
| WO | WO 2016191815 | 12/2016 |
| WO | WO 2017053504 | 3/2017 |

(56) References Cited

FOREIGN PATENT DOCUMENTS

| | | |
|---|---|---|
| WO | WO 2017142948 | 8/2017 |
| WO | WO 2017173493 | 10/2017 |
| WO | WO 2017210352 | 12/2017 |
| WO | WO 2017219096 | 12/2017 |
| WO | WO 2018080753 | 5/2018 |
| WO | WO 2018119220 | 6/2018 |
| WO | WO 2018160992 | 9/2018 |
| WO | WO 2018170141 | 9/2018 |
| WO | WO 2019178634 | 9/2019 |
| WO | WO 2019204884 | 10/2019 |
| WO | WO 2019231796 | 12/2019 |
| WO | WO 2020082118 | 4/2020 |
| WO | WO 2020082126 | 4/2020 |
| WO | WO 2020082128 | 4/2020 |
| WO | WO 2020087123 | 5/2020 |
| WO | WO 2020087135 | 5/2020 |
| WO | WO 2020124135 | 6/2020 |

OTHER PUBLICATIONS

"Battelle Neurotechnology—Moving Beyond The Limits In Neurotechnology", Battelle, www.battelle.org, May 2014, pp. 1-2.
"Evoke 12C Percutaneous Leads", Saluda Medical, specifications available in the Evoke Surgical Guide, version 6, http://www.saludamedical.com/manuals/, retrieved May 2017.
"Haptic technology", VVikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Abrard et al., "A time-frequency blindsignal separation methodapplicable to underdetermined mixtures of dependent sources", Signal Processing 85 (2005) 1389-1403.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al., Muscle Fibre Conduction Velocity in Motor Units of the Human Anterior Tibial Muscle: a New Size Principle Parameter, J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Australian Examination Report for Application No. 2019283936, Mailed Apr. 1, 2021, 7 pages.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R., An Electronic System for Extracellular Neural Stimulation and Recording, Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Bratta et al., "Orderly Stimulation of Skeletal Muscle Motor Units with Tripolar Nerve Cuff Electrode", IEEE Transactions on Biomedical Engineering, vol. 36, No. 8, 1989.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Casey et al., "Separation of Mixed Audio Sources by Independent Subspace Analysis", Mitsubishi Electric Research Laboratories (2001).
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13. No. 2, pp. 161-163.
Dawson, G. D., The relative excitability and conduction velocity of sensory and motor nerve fibres in man, Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Delgado et al., "Measurement and interpretation of electrokinetic phenomena", Pure Appl. Chem., 2005, vol. 77, No. 10, pp. 1753-1805.
Devergnas, A. et al., Cortical potentials evoked by deep brain stimulation in the subthalamic area, Front Syst Neurosci. 2011; 5: 30. May 13, 2011. doi:10.3389/fnsys.2011.00030.
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL., 4 pgs.
Dillier, N. et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge By Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
European Search Report for European Application 12785619.3 Search Completed Oct. 13, 2014, Mailed Oct. 23, 2014, 7 pgs.
European Search Report for European Application 12785669.8 Search Completed Sep. 22, 2014, Mailed Sep. 29, 2014, 5 pgs.
European Search Report for European Application No. 15861444.6, Search completed Jul. 13, 2018, Mailed Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report mailed Dec. 17, 2013, 6 pgs.
Extended European Search Report for European Application No. 13852669.4, Search completed Jun. 8, 2016, Mailed Jun. 22, 2016, 09 Pgs.

(56) References Cited

OTHER PUBLICATIONS

Extended European Search Report for European Application No. 14861553.7, Search completed Jun. 8, 2017, Mailed Jun. 19, 2017, 8 Pgs.
Extended European Search Report for European Application No. 14863597.2, Search completed Jun. 6, 2017, Mailed Jun. 13, 2017, 9 Pgs.
Extended European Search Report for European Application No. 15768956.3, Search completed Oct. 3, 2017, Mailed Oct. 10, 2017, 8 Pgs.
Extended European Search Report for European Application No. 15789515.2, Search completed Dec. 4, 2017, Mailed Jan. 30, 2018, 7 Pgs.
Extended European Search Report for European Application No. 16739680.3, Search completed Jun. 1, 2018, Mailed Jun. 12, 2018, 9 Pgs.
Extended European Search Report for European Application No. 16802237.4, Search completed Dec. 11, 2018, Mailed Dec. 19, 2018, 9 Pgs.
Extended European Search Report for European Application No. 16802238.2, Search completed Oct. 17, 2018, Mailed Oct. 24, 2018, 8 Pgs.
Extended European Search Report for European Application No. 17778477.4, report completed Nov. 12, 2019, mailed Nov. 20, 2019, 7 pgs.
Extended European Search Report for European Application No. 17814341.8, report completed Dec. 12, 2019, report mailed Jan. 2, 2020, 8 pgs.
Extended European Search Report for European Application No. 13853514.1, Search completed Jun. 8, 2016, Mailed Jun. 15, 2016, 07 Pgs.
Extended European Search Report in European Appln No. 18910394.8, dated Oct. 15, 2021, 8 pages.
Extended European Search Report in European Appln No. 19793420.1, dated Dec. 17, 2021, 9 pages.
Extended European Search Report in European Appln No. 19875139.8, dated Jun. 15, 2022, 8 pages.
Extended European Search Report in European Appln No. 19899138.2, dated Aug. 3, 2022, 9 pages.
Fagius, J. et al., "Sympathetic Reflex Latencies and Conduction Velocities in Normal Man", Journal of Neurological Sciences, 1980. vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientific WorldJournal, (2007) 7, pp. 144-160.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Franke, Felix et al., An Online Spike Detection and Spike Classification Algorithm Capable of Instantaneous Resolution of Overlapping Spikes, Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
George et al., "Vagus nerve stimulation: a new tool for brain research and therapy", Biological Psychiatry 47, No. 4, Feb. 15, 2000, pp. 287-295.
Gmel et al., "A new biomarker for closed-loop deep brain stimulation in the subthalamic nucleus for patients with Parkinson's disease," IEEE 2014 Biomedical Circuits and Systems Conference, BioCAS 2014—Proceedings. 500-503. 10.1109/BioCAS.2014.6981772 (abstract only).
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Goodall, E. V., "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.
Gorman et al., "ECAP Mapping of the Spinal Cord: Influence of Electrode Position on Aβ Recruitment", (2012)., In 16th Annual Meeting. Presented at the North American Neuromodulation Society, Las Vegas, NV.
Gorman et al., "Neural Recordings For Feedback Control Of Spinal Cord Stimulation: Reduction Of Paresthesia Variability.", 2013, In International Neuromodulation Society 11th World Congress. Presented at the International Neuromodulation Society 11th World Congress, Berlin, Germany.
Hallstrom et al., "Distribution of lumbar spinal evoked potentials and their correlation with stimulation-induced paresthesiae", (1991), Electroencephalography and clinical neurophysiology 80:126-139.
Harper, A. A. et al., "Conduction Velocity is Related to Morphological Cell Type in Rat Dorsal Root Ganglion Neurones", J. Physiol, (1985), 359, pp. 31-46.
He et al., "Perception threshold and electrode position for spinal cord stimulation", Pain, 59 (1994) 55-63 pages.
Herreras, "Local Field Potentials: Myths and Misunderstandings", Frontiers in Neural Circuits, Dec. 15, 2016, vol. 10, Article 1101, 16 pgs.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 Pages.
Howell et al., "Evaluation of Intradural Stimulation Efficiency and Selectivity in a Computational Model of Spinal Cord Stimulation", PLOS ONE, D01:10.1371/journal.pone.0114938, Dec. 23, 2014.
Huff, Terry B. et al., "Real-Time CARS Imaging Reveals a Calpain-Dependent Pathway for Paranodal Myelin Retraction during High Frequency Stimulation", PLoS ONE vol. 6, issue 3 (Mar. 3, 2011): e17176, 11 pgs.
International Preliminary Report for International Application No. PCT/AU2017/050296, Issued Oct. 9, 2018, 7 Pgs.
International Preliminary Report for International Application No. PCT/AU2017/050647, Issued Dec. 25, 2018, 8 pgs.
International Preliminary Report for International Application No. PCT/AU2019/050384, Mailed Oct. 27, 2020, 8 pgs.
International Preliminary Report on Patentability for International Application No. PCT/AU2011/001127, Report Issued Mar. 5, 2013, 9 pgs.
International Preliminary Report on Patentability for International Application No. PCT/AU2012/000511, Report Issued Nov. 19, 2013, 6 pgs.
International Preliminary Report on Patentability for International Application No. PCT/AU2012/000512, Report Issued Nov. 19, 2013, 8 pgs.
International Preliminary Report on Patentability for International Application No. PCT/AU2012/000513, Report Issued Nov. 19, 2013, 11 pgs.
International Preliminary Report on Patentability for International Application No. PCT/AU2012/000515, Report Issued Nov. 19, 2013, 5 pgs.
International Preliminary Report on Patentability for International Application No. PCT/AU2012/000516, Report Issued Nov. 19, 2013, 9 pgs.

(56) References Cited

OTHER PUBLICATIONS

International Preliminary Report on Patentability for International Application No. PCT/AU2012/000517, Report Issued Nov. 19, 2013, 6 pgs.
International Preliminary Report on Patentability for International Application No. PCT/AU2012/000518, Report Issued Nov. 19, 2013, 11 pgs.
International Preliminary Report on Patentability for International Application No. PCT/AU2012/001441, Report Issued May 27, 2014, 10 pgs.
International Preliminary Report on Patentability for International Application No. PCT/AU2013/001279, Report Issued May 12, 2015, 6 pgs.
International Preliminary Report on Patentability for International Application No. PCT/AU2013/001280, Report Issued May 12, 2015, 6 pgs.
International Preliminary Report on Patentability for International Application No. PCT/AU2014/001049, Report Issued May 17, 2016, 5 pgs.
International Preliminary Report on Patentability for International Application No. PCT/AU2018/050278, Issued Sep. 29, 2020, 7 pgs.
International Preliminary Report on Patentability for International Application No. PCT/AU2014/050369, Report Issued May 24, 2016, 8 pgs.
International Preliminary Report on Patentability for International Application No. PCT/AU2015/050135, Report Issued Oct. 4, 2016, 13 pgs.
International Preliminary Report on Patentability for International Application No. PCT/AU2015/050215, Report Issued Nov. 8, 2016, 4 pgs.
International Preliminary Report on Patentability for International Application No. PCT/AU2015/050422, Report Issued Jan. 31, 2017, 8 pgs.
International Preliminary Report on Patentability for International Application No. PCT/AU2015/050724, Report Issued May 23, 2017, 5 pgs.
International Preliminary Report on Patentability for International Application No. PCT/AU2015/050753, Report Issued Jun. 13, 2017, 7 pgs.
International Preliminary Report on Patentability for International Application No. PCT/AU2015/050787, Report Issued Jun. 13, 2017, 6 pgs.
International Preliminary Report on Patentability for International Application No. PCT/AU2016/050019, Report Issued Jul. 25, 2017, 9 pgs.
International Preliminary Report on Patentability for International Application No. PCT/AU2016/050263, Report Issued Oct. 10, 2017, 9 pgs.
International Search Report & Written Opinion for International Application No. PCT/AU2013/001280, Search Completed Jan. 16, 2014, Mailed Jan. 16, 2014, 8 Pgs.
International Search Report & Written Opinion for International Application PCT/AU2013/001279, Search Completed Jan. 9, 2014, Mailed Jan. 9, 2014, 9 Pgs.
International Search Report and Written Opinion for International Application No. PCT/AU2011/001127, date completed Nov. 11, 2011, date mailed Nov. 15, 2011, 13 pgs.
International Search Report and Written Opinion for International Application No. PCT/AU2012/001441, International Filing Date Nov. 23, 2012, Search Completed Feb. 26, 2013, Mailed Feb. 26, 2013, 14 pgs.
International Search Report and Written Opinion for International Application No. PCT/AU2014/001049, Search completed Feb. 10, 2015, Mailed Feb. 10, 2015, 8 Pgs.
International Search Report and Written Opinion for International Application No. PCT/AU2014/050369, Search completed Feb. 20, 2015, Mailed Feb. 20, 2015, 14 Pgs.
International Search Report and Written Opinion for International Application No. PCT/AU2015/050135, Search completed Jun. 30, 2015, Mailed Jun. 30, 2015, 26 Pgs.
International Search Report and Written Opinion for International Application No. PCT/AU2015/050422, Search completed Oct. 14, 2015, Mailed Oct. 14, 2015, 17 Pgs.
International Search Report and Written Opinion for International Application No. PCT/AU2015/050724, Search completed May 9, 2016, Mailed May 9, 2016, 8 Pgs.
International Search Report and Written Opinion for International Application No. PCT/AU2015/050753, Search completed Feb. 10, 2016, Mailed Feb. 10, 2016, 10 Pgs.
International Search Report and Written Opinion for International Application No. PCT/AU2015/050787, Search completed Mar. 16, 2016, Mailed Mar. 16, 2016, 10 Pgs.
International Search Report and Written Opinion for International Application No. PCT/AU2016/050019, Search completed May 4, 2016, Mailed May 4, 2016, 16 Pgs.
International Search Report and Written Opinion for International Application No. PCT/AU2016/050263, Search completed Nov. 16, 2016, Mailed Nov. 16, 2016, 8 Pgs.
International Search Report and Written Opinion for International Application No. PCT/AU2016/050430, Search completed Aug. 16, 2016, Mailed Aug. 16, 2016, 10 Pgs.
International Search Report and Written Opinion for International Application No. PCT/AU2016/050431, Search completed Aug. 16, 2016, Mailed Aug. 16, 2016, 11 Pgs.
International Search Report and Written Opinion for International Application No. PCT/AU2016/050439, Search completed Jul. 15, 2016, Mailed Jul. 15, 2016, 8 Pgs.
International Search Report and Written Opinion for International Application No. PCT/AU2017/050296, Search completed Jul. 28, 2017, Mailed Jul. 28, 2017, 10 Pgs.
International Search Report and Written Opinion for International Application No. PCT/AU2017/050647, Search completed Sep. 29, 2017, Mailed Sep. 29, 2017, 13 Pgs.
International Search Report and Written Opinion for International Application No. PCT/AU2018/050278, Search completed Jun. 18, 2018, Mailed Jun. 18, 2018, 12 Pgs.
International Search Report and Written Opinion for International Application No. PCT/AU2019/050384, Search completed Jun. 25, 2019, Mailed Jun. 25, 2019, 15 Pgs.
International Search Report and Written Opinion for International Application No. PCT/AU2019/051385, Search completed Mar. 24, 2020, Mailed Mar. 24, 2020, 8 Pgs.
International Search Report and Written Opinion for International Application No. PCT/AU2015/050215, Search completed Jul. 30, 2015, Mailed Jul. 30, 2015, 8 Pgs.
International Search Report for Australian Application 2011901829 Search Completed Feb. 6, 2012, Mailed Feb. 7, 2012, 3 pgs.
International Search Report for International Application No. PCT/AU2019/051151, International Filing Date Oct. 22, 2019, Search Completed Feb. 24, 2020, Mailed Feb. 24, 2020, 9 pgs.
International Search Report for International Application No. PCT/AU2019/051160, International Filing Date Oct. 23, 2019, Search Completed Jan. 28, 2020, Mailed Jan. 28, 2020, 13 pgs.
International Search Report for International Application No. PCT/AU2019/051210, International Filing Date Nov. 2, 2019, Search Completed Feb. 4, 2020, Mailed Feb. 4, 2020, 10 pgs.
International Search Report for International Application No. PCT/AU2012/000511, International Filing Date May 11, 2012, Search Completed May 17, 2012, Mailed May 18, 2012, 4 pgs.
International Search Report for International Application No. PCT/AU2012/000512, International Filing Date May 11, 2012, Search Completed Jul. 10, 2012, Mailed Jul. 11, 2012, 4 pgs.
International Search Report for International Application No. PCT/AU2012/000513, International Filing Date May 11, 2012, Search Completed May 29, 2012, Mailed May 30, 2012, 5 pgs.
International Search Report for International Application No. PCT/AU2012/000515, International Filing Date May 11, 2012, Search Completed May 21, 2012, Mailed Jun. 4, 2012, 5 pgs.
International Search Report for International Application No. PCT/AU2012/000516, International Filing Date May 11, 2012, Search Completed Jul. 11, 2012, Mailed Jul. 12, 2012, 8 pgs.

(56) References Cited

OTHER PUBLICATIONS

International Search Report for International Application No. PCT/AU2012/000517, International Filing Date May 11, 2012, Search Completed Jun. 4, 2012, Mailed Jun. 6, 2012, 3 pgs.
International Search Report for International Application No. PCT/AU2012/000518, International Filing Date May 11, 2012, Search Completed Jun. 8, 2012, Mailed Jun. 12, 2012, 4 pgs.
International Search Report for International Application No. PCT/AU2019/051163, International Filing Date Oct. 23, 2019, Search Completed Jan. 21, 2020, Mailed Jan. 31, 2020, 8 pgs.
International Search Report for International Application No. PCT/AU2019/051197, International Filing Date Oct. 30, 2019, Search Completed Jan. 21, 2020, Mailed Jan. 21, 2020, 15 pgs.
International Type Search Report for International Application No. AU 2015902393, Search completed May 16, 2016, Mailed May 16, 2016, 8 Pgs.
Islam et al., "Methods for artifact detection and removal from scalp EEG: A review," Neurophysiologie Clinique—Clinical Neurophysiology, Oct. 2016, 46(4): 287-305.
Jang et al, "Single Channel Signal Separation Using Time-Domain Basis Functions", IEEE Signal Processing Letters, Jun. 2003, vol. 10, No. 6.
Jang et al., "A Maximum Likelihood Approach to Single-channel Source Separation", Journal of Machine Learning Research 4 (2003) 1365-1392.
Japanese Office Action for Application No. 2017-546830, Mailed Feb. 20, 2020, 5 pages with English translation.
Japanese Office Action for Application No. 2017-553090, Mailed Mar. 16, 2020, 12 pages with English translation.
Japanese Office Action for Application No. 2018-552138, Mailed Mar. 1, 2021, 7 pages with English translation.
Japanese Office Action for Application No. 2018-513699, Mailed Jun. 8, 2020, 7 pages with English translation.
Jeffrey et al., "A reliable method for intracranial electrode implantation and chronic electrical stimulation in the mouse brain", BMC Neuroscience. Biomed Central. London. GB. vol. 14. No. 1. Aug. 6, 2013 (Aug. 6, 2013) • p. 82.
Jones et al., "Scaling of Electrode—Electrolyte Interface Model Parameters In Phosphate Buffered Saline", IEEE Transactions on Biomedical Circuits and Systems, 2015, vol. 9, No. 3, pp. 441-448.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
Kent, "Characterization of Evoked Potentials During Deep Brain Stimulation in the Thalamus", Dissertation, Duke University. Retrieved from https://hdl.handle.net/10161/8195, 2013.
Kent, Ar et al., "Recording evoked potentials during deep brain stimulation: development and validation of instrumentation to suppress the stimulus artefact", J Neural Eng. Jun. 2012; 9(3):036004, Apr. 18, 2012. doi: 10.1088/1741-2560/9/3/036004.
Kim et al., "A Wavelet-Based Method for Action Potential Detection From Extracellular Neural Signal Recording VVith Low Signal-to-Noise Ratio", IEEE Transactions On Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.
Kopelman et al., Attempted Reversible Sympathetic Ganglion Block by An Implantable Neurostimulator, Interactive Cardio Vascular and Thoracic Surgery, Feb. 7, 2012, vol. 14, Issue 5, pp. 605-609, doi:10.1093/icvts/ivr137.
Krames et al., "Neuromodulation", 1st Edition, Academic Press, 2009, p. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Laird-Wah, "Improving Spinal Cord Stimulation: Model-Based Approaches to Evoked Response Telemetry", UNSW, Aug. 2015.
Lempka, Scott, The Electrode-Tissue Interface During Recording and Stimulation In The Central Nervous System, published on May 2010, 155 pgs.
Levy et al., "Incidence and Avoidance of Neurologic Complications with Paddle Type Spinal Cord Stimulation Leads", Neuromodulation 14(15), Sep. 2011, pp. 412-422.
Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mahnam et al., "Measurement of the current-distance relationship using a novel refractory interaction technique", J. Neural Eng. 6(2): 036005, published May 20, 2009, 22 pgs.
Mannan et al., Identification and Removal of Physiological Artifacts From Electroencephalogram Signals: A Review, IEEE Access, May 31, 2018, vol. 6, pp. 30630-30652, https://doi.org/10.1109/ACCESS.2018.2842082.
Markandey, Vishal, "ECG Implementation on the TMS320C5515 DSP Medical Development Kit (MDK)", Texas Instruments Application Report Jun. 2010, 35 pgs.
Massachusetts Institute of Techn, The Compound Action Potential of the Frog Sciatic Nerve, Quantitative Physiology: Cells and Tissues. Fall, 1999, Retrieved from http://umech.mit.edu/freeman/6.021J/2001/Iab.pdf on May 22, 2012.
Matzner et al., "Na+ Conductance and the Threshold for Repetitive Neuronal Firing", Brain Research 597, No. 1 (Nov. 27, 1992): 92-98, doi:10.1016/0006-8993(92)91509-D.
Mcgill, Kevin et al., On the Nature and Elimination of Stimulus Artifact in Nerve Signals Evoked and Recorded Using Surface Electrodes, IEEE Transactions On Biomedical Engineering, vol. BME-29, No. 2, Feb. 1982, pp. 129-137.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm,, Capture Date Jul. 9, 2012, Printed on May 11, 2017.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Melzack et al., "Pain mechanisms: a new theory", Science, New York, New York, vol. 150, No. 3699, Nov. 19, 1965, pp. 971-979.
Miles et al., An Electrode for Prolonged Stimulation of the Brain, Proc. 8th Meeting World Soc. Stereotactic and Functional Neurosurgery, Part III, Zurich, 1981, Appl. Neurophysiol, 45, 1982, pp. 449-445.
Misawa et al., Neuropathic Pain Is Associated with Increased Nodal Persistent Na(+) Currents in Human Diabetic Neuropathy, Journal of the Peripheral Nervous System: JPNS, 14, No. 4 (Dec. 2009): 279-284.

(56) References Cited

OTHER PUBLICATIONS

Niazy et al., "Removal of FM RI environment artifacts from EEG data using optimal basis sets", NeuroImage 28 (2005) 720-737.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Office Action for Chinese Patent Application No. 201680020725.4, dated Mar. 16, 2020, 8 pgs.
Oh et al., "Long-term hardware-related complications of deep brain stimulation", Neurosurgery, vol. 50, No. 6, Jun. 2002, pp. 1268-1274, discussion pp. 1274-1276.
Olin et al., "Postural Changes in Spinal Cord Stimulation Perceptual Thresholds", Neuromodulation, vol. 1, No. 4, 1998, pp. 171-175.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al., "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., Closing the Loop in Neuromodulation Therapies: Spinal Cord Evoked Compound Action Potentials During Stimulation for Pain Management (230)., 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Parker et al., "Electrically Evoked Compound Action Potentials Recorded From the Sheep Spinal Cord", Neuromodulation, vol. 16, 2013, pp. 295-303.
Partial European Search Report for European Application No. 16775966.1, Search completed Oct. 26, 2018, Mailed Nov. 6, 2018, 11 Pgs.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Peterson et al., "Stimulation artifact rejection in closed-loop, distributed neural interfaces", ESSCI RC, 42nd European Solid-State Circuits Conference, Lausanne, 2016, pp. 233-235.
Rattay, "Analysis of Models for External Stimulation of Axons", IEEE Transactions On Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Ross et al., "Improving Patient Experience with Spinal Cord Stimulation: Implications of Position-Related Changes in Neurostimulation", Neuromodulation 2011; e-pub ahead of print. DOI:10.1111/j.1525-1403.2011.00407.x 6 pages.
Roy, S. H. et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S., Electrode/Electrolyte Interfaces: Structure and Kinetics of Charge Transfer, Fuel Cells, 2006, Chapter 2, 67 Pages.
Stanslaski et al., "Design and Validation of a Fully Implantable, Chronic, Closed-Loop Neuromodulation Device with Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Struijk et al., Paresthesia Thresholds in Spinal Cord Stimulation: A Comparison of Theoretical Results with Clinical Data, IEEE Transactions on Rehabilitation Engineering, vol. 1, No. 2, Jun. 1993, pp. 101-108.
Struijk, The Extracellular Potential of a Myelinated Nerve Fiber in an Unbounded Medium and in Nerve Cuff Models, Biophysical Journal vol. 72 Jun. 1997 2457-2469.
Sufka et al., "Gate Control Theory Reconsidered", Brain and Mind, 3, No. 2, 2002, pp. 277-290.
Takahashi et al, "Classification of neuronal activities from tetrode recordings using independent component analysis", Neurocomputing, (2002), vol. 49, Issues 1-4, 289-298.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.

(56) References Cited

OTHER PUBLICATIONS

Van Den Berg et al., "Nerve fiber size-related block of action currents by phenytoin in mammalian nerve", Epilepsia, Nov. 1994, 35(6), pp. 1279-1288.

Villavicencio, Alan T., "Laminectomy versus Percutaneous Electrode Placement for Spinal Cord Stimulation," Neurosurgery, vol. 46 (2), Feb. 2000, pp. 399-405.

Vleggeert, Lankamp et al., "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

Woessner, "Blocking Out the Pain, Electric Nerve Block Treatments for Sciatic Neuritis", Retrieved from: http://www.practicalpainmanagement.com/pain/spine/radiculopathy/blocking-outpain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.

Written Opinion for International Application No. PCT/AU2012/000511, International Filing Date May 11, 2012, Search Completed May 17, 2012, Mailed May 18, 2012, 5 pgs.

Written Opinion for International Application No. PCT/AU2012/000512, International Filing Date May 11, 2012, Search Completed Jul. 10, 2012, Mailed Jul. 11, 2012, 7 pgs.

Written Opinion for International Application No. PCT/AU2012/000513, International Filing Date May 11, 2012, Search Completed May 29, 2012, Mailed May 30, 2012, 10 pgs.

Written Opinion for International Application No. PCT/AU2012/000515, International Filing Date May 11, 2012, Search Completed May 21, 2012, Mailed Jun. 4, 2012, 4 pgs.

Written Opinion for International Application No. PCT/AU2012/000516, International Filing Date May 11, 2012, Search Completed Jul. 11, 2012, Mailed Jul. 12, 2012, 8 pgs.

Written Opinion for International Application No. PCT/AU2012/000517, International Filing Date May 11, 2012, Search Completed Jun. 4, 2012, Mailed Jun. 6, 2012, 5 pgs.

Written Opinion for International Application No. PCT/AU2012/000518, International Filing Date May 11, 2012, Search Completed Jun. 8, 2012, Mailed Jun. 12, 2012, 10 pgs.

Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.

Xie et al., Functional Changes in Dorsal Root Ganglion Cells after Chronic Nerve Constriction in the Rat, Journal of Neurophysiology 73, No. 5 (May 1, 1995): 1811-1820.

Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.

Yamada et al., "Extraction and Analysis of the Single Motor Unit F-Wave of the Median Nerve", EMG Methods for Evaluating Muscle and Nerve Function, InTech, 2012, 15 pgs.

Yearwood, T. L., "Pulse VVidth Programming in Spinal Cord Stimulation: a Clinical Study", Pain Physician. 2010. vol. 13, pp. 321-335.

Yingling et al., Use of Antidromic Evoked Potentials in Placement of Dorsal Cord Disc Electrodes, Applied Neurophysiology, 1986, vol. 49, pp. 36-41.

Yuan, S. et al., Recording monophasic action potentials using a platinumelectrode ablation catheter, Europace. Oct. 2000; 2(4):312-319.

Zhang et al., "Automatic Artifact Removal from Electroencephalogram Data Based on A Priori Artifact Information", BioMed research international. 2015. 720450. Aug. 25, 2015 DOI:https://doi.org/10.1155/2015/720450.

Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

\* cited by examiner

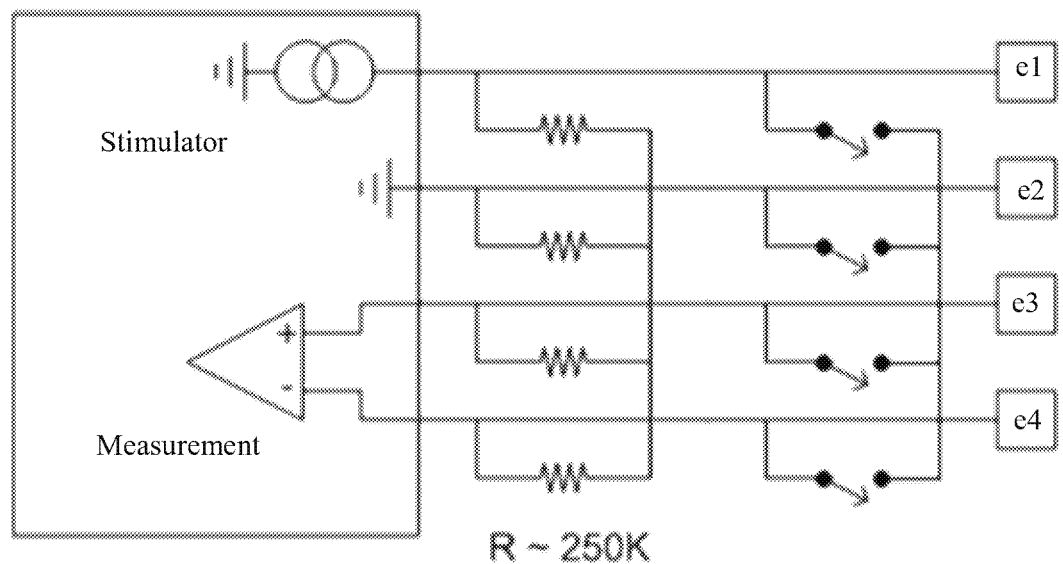
Figure 1 – Prior Art
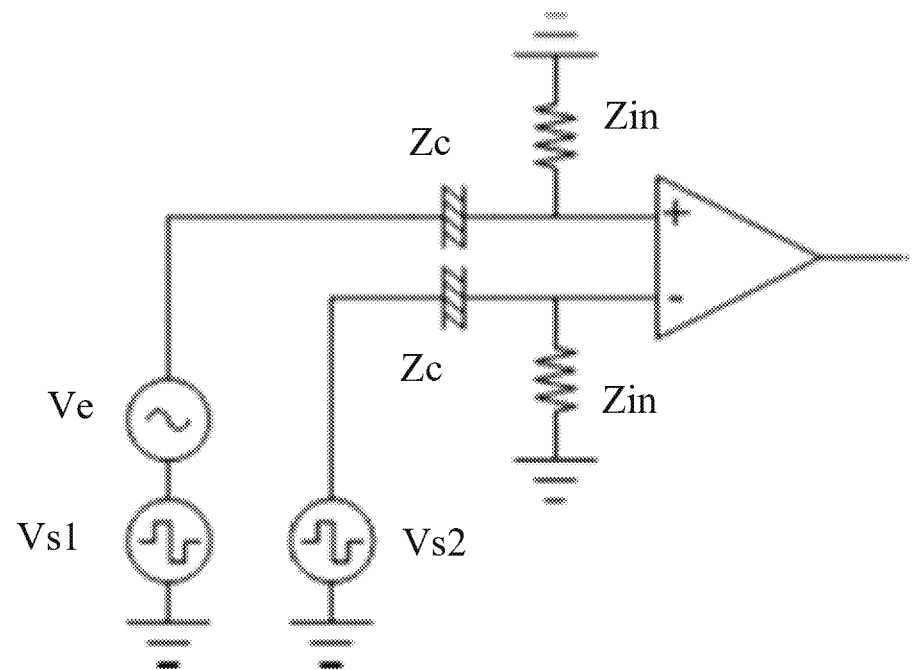
Figure 2

NEURAL MEASUREMENT

CROSS-REFERENCE TO RELATED APPLICATIONS

This application is a continuation of U.S. patent application Ser. No. 16/532,364, filed Aug. 5, 2019, which is a continuation of U.S. patent application Ser. No. 15/307,770, filed Oct. 28, 2016, which is a 371 application of International Patent Application PCT/AU2015/050215, filed on May 5, 2015, which claims the benefit of Australian Provisional Patent Application No. 2014901639, filed May 5, 2014, all of which applications are incorporated herein by reference in their entirety.

TECHNICAL FIELD

The present invention relates to measurement of neural activity, and in particular relates to measurement of a compound action potential or the like by using one or more electrodes implanted proximal to neural tissue.

BACKGROUND OF THE INVENTION

There are a range of circumstances in which it is desirable to obtain an electrical measurement of a compound action potential (CAP) evoked on a neural pathway by an electrical stimulus applied to the neural pathway. However, this can be a difficult task as an observed CAP signal will typically have a maximum amplitude in the range of microvolts, whereas a stimulus applied to evoke the CAP is typically several volts. Electrode artefact usually results from the stimulus, and manifests as a decaying output of several millivolts throughout the time that the CAP occurs, presenting a significant obstacle to isolating the CAP of interest. As the neural response can be contemporaneous with the stimulus and/or the stimulus artefact, CAP measurements present a difficult challenge of amplifier design. In practice, many non-ideal aspects of a circuit lead to artefact, and as these mostly have a decaying exponential characteristic which can be of either positive or negative polarity, identification and elimination of sources of artefact can be laborious.

A number of approaches have been proposed for recording a CAP, including those of King (U.S. Pat. No. 5,913,882), Nygard (U.S. Pat. No. 5,758,651) and Daly (US Patent Application No. 2007/0225767).

Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, data can be obtained. This is the case in surgical monitoring where there are large distances between the stimulating and recording electrodes so that the propagation time from the stimulus site to the recording electrodes exceeds 2 ms. However, to characterize the responses from the dorsal columns for example, high stimulation currents and close proximity between electrodes are required, and therefore the measurement process must overcome contemporaneous artifact directly. Similar considerations can arise in deep brain stimulation where it can be desirable to stimulate a neural structure and immediately measure the response of that structure before the neural response propagates elsewhere.

Implanted electrical stimulus devices must also provide for charge recovery in order to ensure that transient currents delivered by stimuli do not lead to a net DC injection of charge into the tissue. One approach is to provide capacitors in series on each electrode, to prevent DC transfer to tissue, and such capacitors are often a requirement of regulatory bodies in order for an active implantable device to obtain market approval. Another arrangement as shown in FIG. 1 omits electrode capacitors, and instead provides switches to short circuit the stimulus and sense electrodes e1-e4 to each other to effect charge recovery between stimuli, and also provides a star network of resistors each of a value in the range of perhaps hundreds of $k\Omega$, permanently connecting all electrodes together in order to equilibrate charge before the device is powered on, as shown in FIG. 1. However, the provision of electrode capacitors or a star network of resistors between the electrodes and the measurement amplifier can give rise to considerable effects of artefact which can interfere with attempts to measure small CAP signals.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method for measuring a neural response to a stimulus, the method comprising:

applying an electrical stimulus from stimulus electrodes to neural tissue;

imposing a delay during which the stimulus electrodes are open circuited; and during the delay, measuring a neural response signal present at sense electrodes with a measurement amplifier, while ensuring that an impedance between the sense electrodes is sufficiently large that a voltage arising on the sense electrode tissue interface in response to the stimulus is constrained to a level which permits assessment of the neural response voltage seen at the sense electrode.

According to a second aspect the present invention provides an implantable device for measuring a neural response to a stimulus, the device comprising:

a plurality of electrodes including one or more nominal stimulus electrodes and one or more nominal sense electrodes;

a stimulus source for providing a stimulus to be delivered from the one or more stimulus electrodes to neural tissue in order to evoke a neural response;

a measurement amplifier for amplifying a neural response signal sensed at the one or more sense electrodes, wherein an impedance between the sense electrodes is sufficiently large that a voltage arising on the sense electrode tissue interface in response to the stimulus is constrained to a level which permits assessment of the neural response voltage seen at the sense electrode; and a control unit configured to control application of a stimulus to the neural tissue and measurement of an evoked neural response, the control unit configured to apply an electrical stimulus from the stimulus electrodes to neural tissue, the control unit further configured to impose a delay during which the stimulus electrodes are open circuited, and the control unit further configured to, during the delay, measure a neural response signal present at the sense electrodes with the measurement amplifier.

It is to be noted that different embodiments may involve stimuli of varying intensity or duration, electrodes of varying geometry and size, and/or a varying spatial separation between the stimulus electrodes and the sense electrode(s). The present invention recognises that knowledge of each such parameter in an evoked response measurement system enables a determination to be made as to an expected voltage which will arise on the sense electrode(s) as a result of the electrical characteristics of the stimulus delivered. In particular, modelling the interface between the sense electrode(s) and the tissue as including a constant phase element impedance, representing the electrode-electrolyte interface capacitance and tissue capacitance, and determining the impedance of the constant phase element for the physical parameters of the implant concerned, enables an appropriate lower limit to be placed on the impedance between the sense electrodes.

The impedance between the sense electrodes is preferably chosen to be sufficiently large that the voltage arising on the sense electrode tissue interface in response to the stimulus is constrained to a level which is no more than 15 times larger than the neural response voltage seen at the sense electrode, more preferably is no more than 5 times larger than the neural response voltage seen at the sense electrode, more preferably is no more than 2 times larger than the neural response voltage seen at the sense electrode, even more preferably is no more than the same as the neural response voltage seen at the sense electrode, and most preferably is no more than half of the neural response voltage seen at the sense electrode.

Some embodiments may utilise a differential measurement of the neural response by using two sense electrodes. In such embodiments the voltage arising on the sense electrode tissue interface in response to the stimulus is to be understood to be the differential voltage arising between the two sense electrodes in response to the stimulus. The two sense electrodes for example may be mounted upon a single implanted electrode array. Alternative embodiments may undertake a single ended measurement utilising a single sense electrode and a distal reference electrode, and in such embodiments the voltage arising on the sense electrode tissue interface in response to the stimulus is to be understood to be the differential voltage arising between the sense electrode and the reference electrode in response to the stimulus.

Some embodiments of the present invention further comprise a sense electrode capacitor provided in series between the sense electrode and the measurement amplifier, the sense electrode capacitor being chosen to have a capacitance which ensures that the voltage arising across the capacitor in response to the stimulus is constrained to a level which permits assessment of the neural response voltage seen at the sense electrode. Such embodiments may thus enable improved prevention of DC charge injection to the tissue, while nevertheless retaining neural response measurement capability. In such embodiments, the stimulus electrodes may have corresponding capacitors in order to prevent DC charge injection, and also to permit electrical reconfiguration of each electrode as either a stimulus electrode or sense electrode, as required.

In some embodiments, the input impedance to the measurement amplifier ($Z_{IN}$) is defined as:

$$Z_{IN} > Z_C \frac{(V_{S1} - V_{S2})}{V_E}$$

where
$Z_C$ is the constant phase element impedance of the or each sense electrode,
$V_{s1}-V_{s2}$ is the differential voltage arising on the sense electrode tissue interface
in response to the stimulus, and
$V_E$ is the neural response voltage seen at the sense electrode.

In such embodiments $Z_{IN}$ may comprise resistance and/or capacitance provided the above requirement is met. To give sufficient margin of $V_E$ over $(V_{s1}-V_{s2})$, in some embodiments $Z_{IN}$ may be limited by:

$$Z_{IN} > A \times Z_C (V_{s1}-V_{s2})/V_E$$

A is a scalar provided to give sufficient margin of $V_E$ over $(V_{s1}-V_{S2})$, and may for example be in the range of 2-5. Alternatively, in embodiments utilising artefact compensation by way of exponential subtraction, A may be in the range of 0.5 or greater while still permitting assessment of the neural response and such embodiments are thus within the scope of the present invention. Moreover, some embodiments may correlate the measurement against a filter template to extract the neural response from the measurement, in accordance with the teachings of Australian Provisional Patent Application No. 2013904519 by the present applicant, the content of which is incorporated herein by reference, and in such embodiments A may be in the range of 0.067 or greater while still permitting assessment of the neural response and such embodiments are thus within the scope of the present invention.

The neural response measurement may in some embodiments be conducted in the manner taught by International Patent Publication No. WO2012155183, the content of which is incorporated herein by reference.

The method may further comprise obtaining neural measurements repeatedly over time and monitoring for changes. In response to detected changes some embodiments may provide feedback control of a therapy delivered to the patient, such as an electrical stimulus therapy and/or medication. Medication may be controlled automatically by an implanted drug pump or by producing a report for a physician to alter a prescription, for example.

In some embodiments, charge on the stimulus electrodes may be recovered by connecting the stimulus electrodes to each other by either a short circuit or via an impedance, before application of the stimulus and/or after measurement of the neural response.

In some embodiments, the measurement amplifier is kept connected to the sense electrodes throughout the stimulus and measurement. In such embodiments, the measurement amplifier is preferably a wide bandwidth amplifier with sufficient common mode range to avoid saturation by the stimulus. Alternatively, the amplifier may be used in an auto-zero state in which it can zero sufficiently quickly after the stimulus to track the neural response.

BRIEF DESCRIPTION OF THE DRAWINGS

An example of the invention will now be described with reference to the accompanying drawings, in which:

FIG. 1 illustrates a prior art approach to neural response measurement;

FIG. 2 illustrates a neural response measurement system in accordance with one embodiment of the present invention;

DESCRIPTION OF THE PREFERRED EMBODIMENTS

FIG. 2 illustrates a neural response measurement system in accordance with one embodiment of the present invention. Two sense electrodes each having a constant phase element (CPE) impedance of $Z_C$ are used to detect a neural response signal Ve arising in neural tissue of an implant recipient. A stimulus applied by stimulus electrodes of the implant (shown in FIG. 4) gives rise to the neural response, but also causes stimulus voltages $V_{s1}$ and $V_{s2}$ to be present on the sense electrodes. An input impedance of $Z_{in}$ is present at each input of the differential measurement amplifier.

The input impedance required in this embodiment of the invention is determined by noting that noise input is comparable to stimulation voltage, and that the goal is for the stimulus to induce a voltage $(V_{s1} - V_{s2})$ on the CPE of the sense electrodes which is less than the evoked response $V_E$. Consequently the desired input impedance is given by:

$$Z_{IN} > Z_C \frac{(V_{S1} - V_{S2})}{V_E}$$

In one embodiment, being a spinal cord stimulator (SCS) having electrodes with an area of 14 mm², $Z_c=20\Omega$, (Vs1−Vs2)~1V, $V_e$=50 uV, so that the above equation dictates that the minimum value of $Z_{in}$ is 400 kΩ To give a sufficient margin of $V_e$ over artefact, a more desirable value of $Z_{in}$ is larger, perhaps in the range 1-2 MΩ. In alternative embodiments such as a cochlear implant with electrode area of about 0.1 mm², being a fraction of the area of an SCS electrode, the minimum required amplifier input impedance is many times higher; 8 MΩ or for sufficient margin more preferably 20 MΩ, illustrating the difficulties of the resistance values chosen in FIG. 1.

Figure 3:
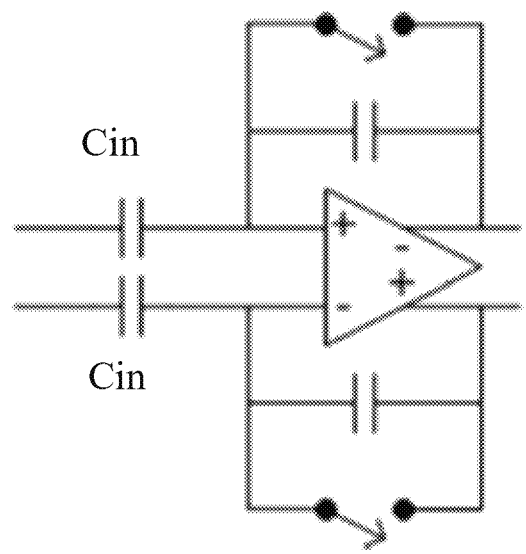
FIG. 3 illustrates an embodiment of the invention utilising electrode capacitors.

FIG. 3 shows an embodiment of the present invention utilising an ASIC amplifier having a very high value of Zin. Electrode capacitors are provided to block DC insertion to the tissue, the electrode capacitors having a value of $C_{in}$=5 pF. Since the ASIC amplifier of FIG. 3 automatically settles to zero during off periods there is no need for resistance to be added at the amplifier input.

Figure 4:
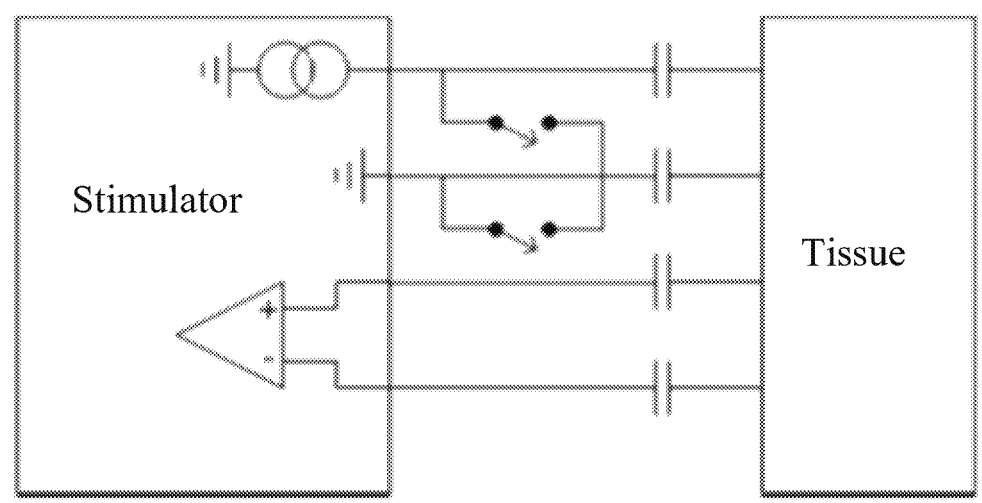
FIG. 4 is another illustration of the embodiment of FIG. 3, showing the stimulus electrode shorting arrangement.

FIG. 4 is another illustration of the embodiment of FIG. 2. Electrode capacitors are provided on all electrodes to block DC. The electrode capacitors can store their own charge which in turn can produce uncontrolled current on switch-on. Accordingly, the control module closes the switches to equilibrate the stimulus electrodes prior to each stimulus. The switches are closed only in short bursts so that the equilibration current does not rise to a level which is perceivable by the implant recipient. Similar embodiments may be provided having additional resistance and/or capacitance on the inputs of the measurement amplifier, so long as the input impedance obeys the equation above.

Figure 5:
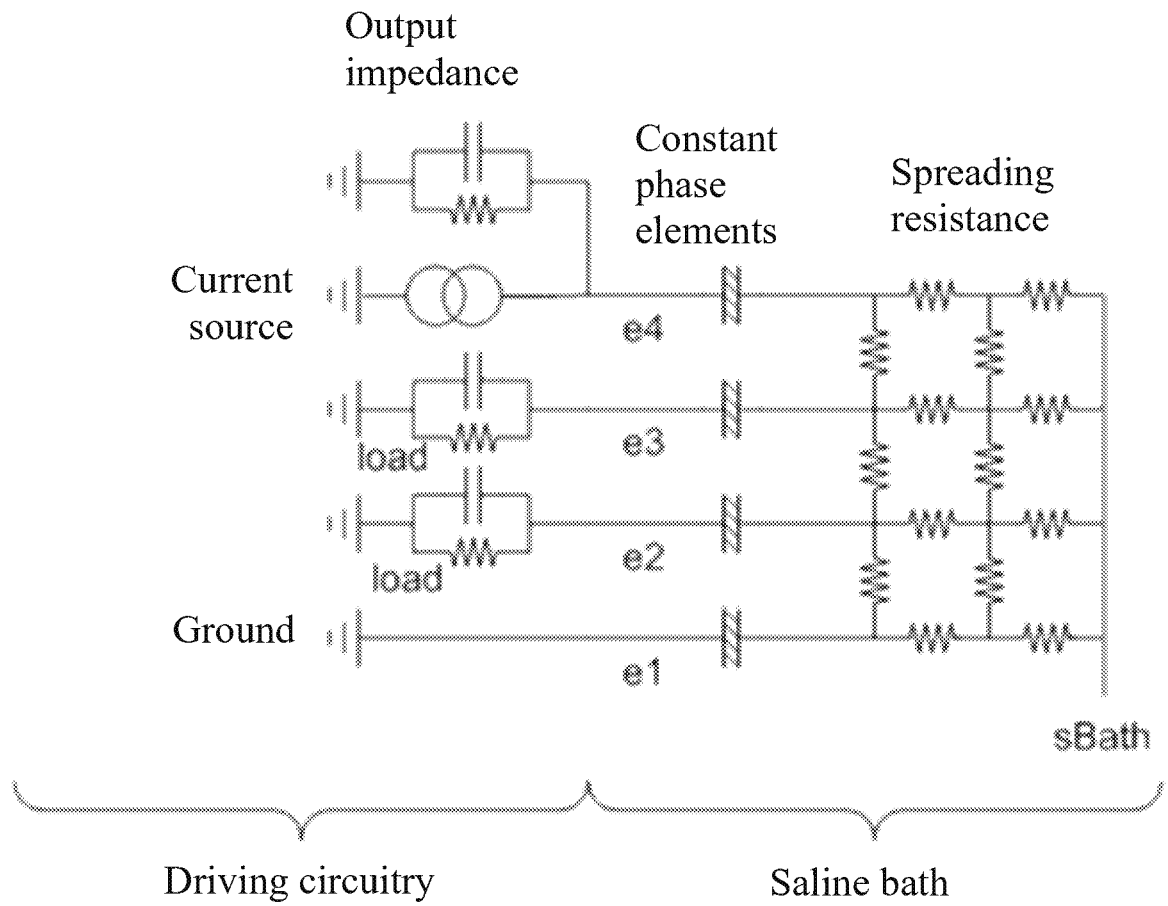
FIG. 5 is a simplified model of the driving circuitry of an implantable device and the surrounding tissue.

The importance of including the constant phase element model of the electrode-to-tissue interface in FIG. 2 for example arises from a simplified model of the driving circuitry and saline as shown in FIG. 5. The circuit consists of the spreading resistance, being a mesh of resistors that model the current through the bulk saline; the constant phase elements (CPE) where the saline meets the electrode metal; an excitation source having an output impedance including some stray capacitance; loading on each electrode and a ground connection. The saline bath has a bulk voltage point sBath. The saline bath is used to mimic tissue. In FIG. 5 a single-ended measurement can be made between electrodes e1 and e2, and a differential measurement can be made between e2 and e3.

Figure 6:
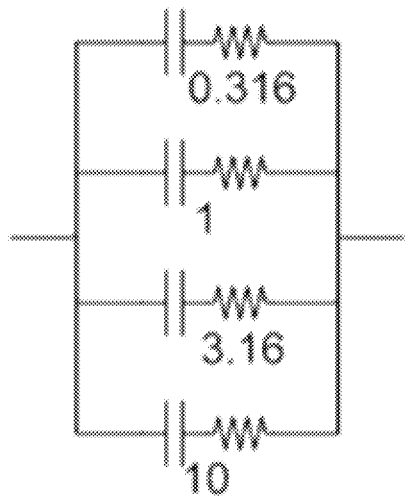
FIG. 6 is an illustrative equivalent circuit of the constant phase element at each electrode-tissue interface.

An equivalent circuit of a CPE is shown in FIG. 6. It consists of a set of series RC networks connected in parallel. To adequately model a saline bath, the CPE might have 20-30 RC pairs, but the simplified version of FIG. 6 is shown for understanding. The RC pairs have time constants that change exponentially, in this case by a factor of sqrt(10), however the notable fact is that the time constants of each RC pair are different from all other RC pairs in the CPE. Following a stimulus, the output voltage of a CPE will change over time as charge redistributes between the capacitors, even though no net current is flowing in or out. This property is shared by a single parallel RC network, although a CPE has no R value that can be found at DC.

Unlike an RC network that shows a response characteristic of the circuit, the response of a CPE is dominated by the RC networks that have a similar time constant to that of the length of the stimulation. For example a SCS may have a stimulus pulse width in the range of 100-500 μs. This result is important for defining the apparent conductance of a capacitor as discussed below.

Following a stimulus, there are three mechanisms or sources of artifact that can be identified in the circuit of FIG. 5. For each of these mechanisms, the load and current source impedances are considered infinite unless otherwise noted:

The voltage on the CPE on electrode 1 changes. This can be seen in a single ended measurement e2-e1, or on the stimulating electrode e1. This is not seen in the differential measurement as this voltage is common mode between e2 and e3.

If the current source output impedance is finite, the change in the electrode 1 CPE voltage causes a current to flow through the spreading resistance. This appears differentially on electrodes e2 and e3. This only occurs due to the mesh nature of the spreading resistance; if modelled by a star resistor or a single string of resistors this will not be observed.

If the input impedance of either sense amplifier is finite, then during stimulus current will flow into this load. This will then settle.

The ability of the model of FIG. 5 to predict the voltage on e4 was experimentally tested. All stimulation used 4 mA 400 us biphasic pulses. These were used to give rise to an artifact large enough to resolve above noise, and with a voltage on the electrodes that could be digitized without anomaly. This stimulation level delivers 1.6 uC per stimulus, which is in the upper end of the range of charge required for comfort level stimulation in a SCS. Measurements were averaged over 99 iterations. As artefact can take many different profiles of either polarity, a single artefact measure was defined as being the integral of the V.t product of the signal, after resetting the DC value to a baseline.

Figure 7:
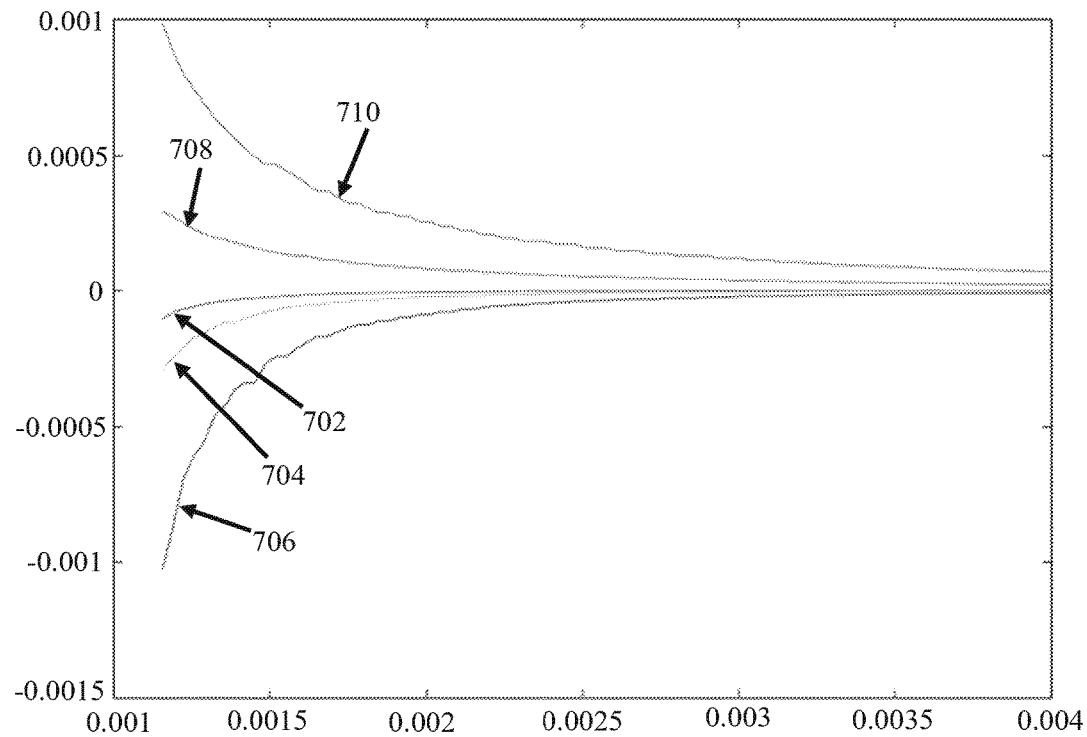
FIG. 7 is a plot produced by a simulation of the model of FIG. 5, showing the artifact arising after a stimulus in the presence of various values of amplifier input impedance, both capacitive and resistive.

In addition to experimental verification a simulation of FIG. 5 was conducted. FIG. 7 shows a simulation output showing the artifact over a selected range after the stimulus, in which the y-axis indicates RMS voltage×time, and the x-axis indicates admittance, with admittance of capacitances being calculated as Y=C·t, where t is the stimulus pulse width. Input impedance on the amplifier was selected to be either 330 pF, 1000 pF, 3300 pF, 330 kΩ, and 100 kΩ, giving rise to respective artefact waveforms 702, 704, 706, 708, 710. It is notable that capacitance and resistance give rise to artefact of opposite polarity. Although these are simple waveforms, in practice there can be several sources of artifact with different time-constants so that the actual artefact seen can be more complex than the simple monotic decreasing curves shown.

Figure 8:
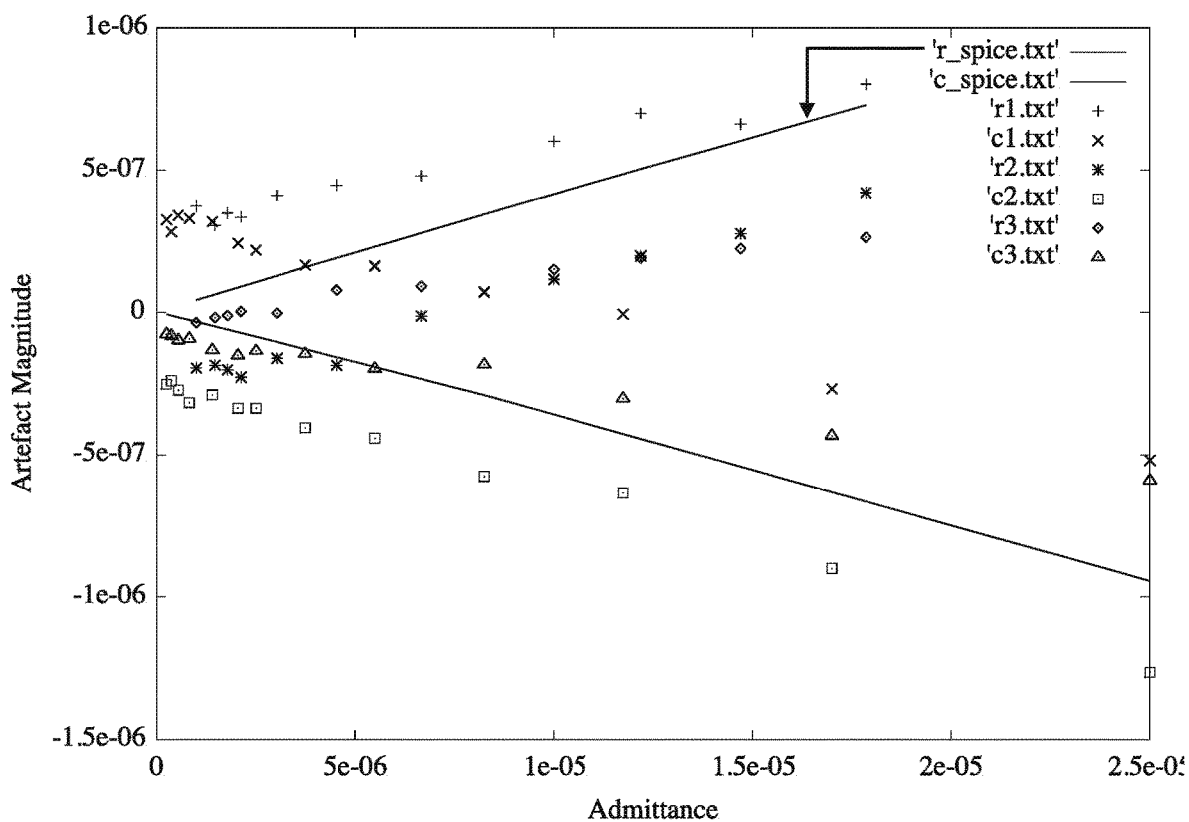
FIG. 8 shows experimental data points, and simulation curves, of artefact arising from a stimulus when the amplifier input resistance and capacitance are varied.

FIG. 8 shows both experimental data points and simulation curves, where the load resistance and capacitance are varied. The conductance of the capacitors, being their value divided by the length of each phase of the biphasic pulse, is a measure that has the same slope of artefact as for a resistor, and is thus preferred to using the entire length of the stimulus in FIGS. 8 to 11. The simulated line and the experimentally obtained data point groups having a positive slope in FIG. 8 show the effect of adding resistance, while the simulated line and the experimentally obtained data point groups having a negative slope show the effect of adding capacitance to the amplifier input impedance. The slopes of the capacitive and resistive lines are very similar for all electrodes, and closely match that of the simulation, indicating that the model of FIG. 5 is largely correct. The electrodes have different y-intercepts. Electrode 1 (the 'r1.txt' data points) has a peak artifact of 700 uV when a resistive load is reduced, which is a very large artefact and would certainly obscure a neural response signal of around 10 uV. In the absence of loading, artifact can be positive or negative. The y-intercept offsets are outside the control of the electronics, and must be handled by techniques such as filtering.

While the plot of FIG. 8 validates the simulation model, it also shows that there is a missing element that causes artifact in the absence of loading and causes the y-intercept offsets. The y-intercept offsets vary from one electrode to the next, and is perhaps the result of metallic contamination on each electrode surface creating a small galvanic cell and asymmetric behaviour for the phases of the biphasic pulse.

Figure 9:
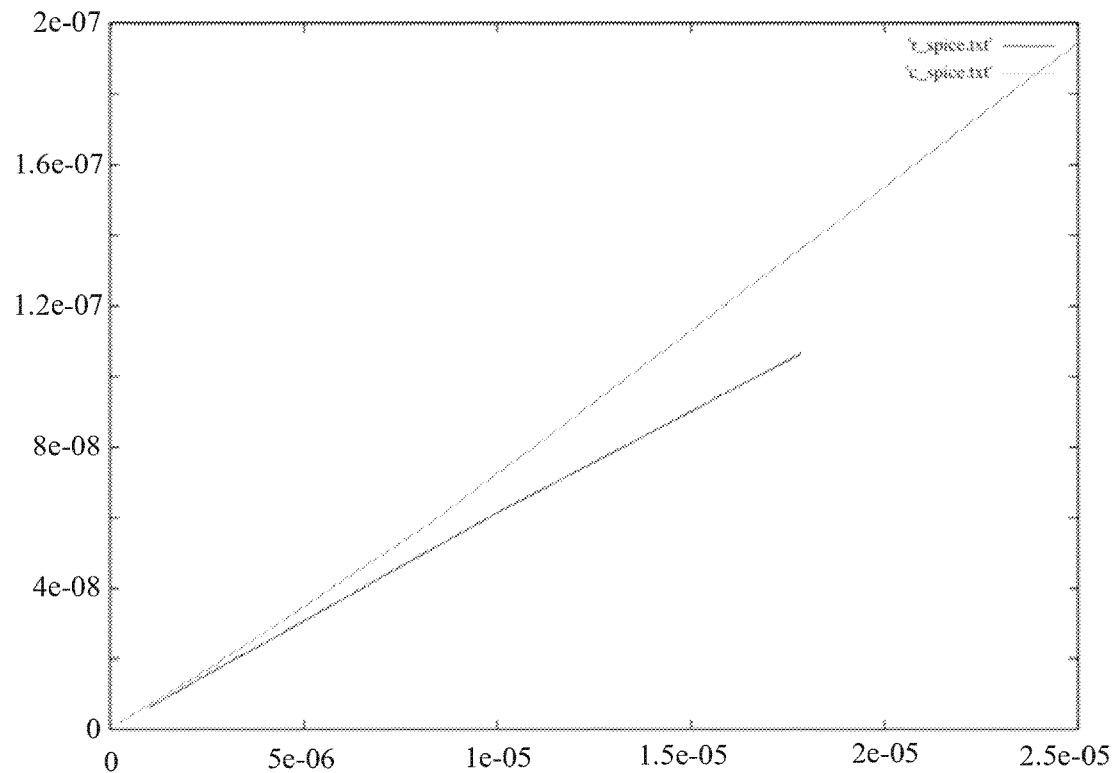
FIG. 9 shows the RMS artifact contribution from resistance and capacitance respectively.

FIG. 9 shows the RMS contribution to simulated artefact from resistance and capacitance respectively.

Figure 10:
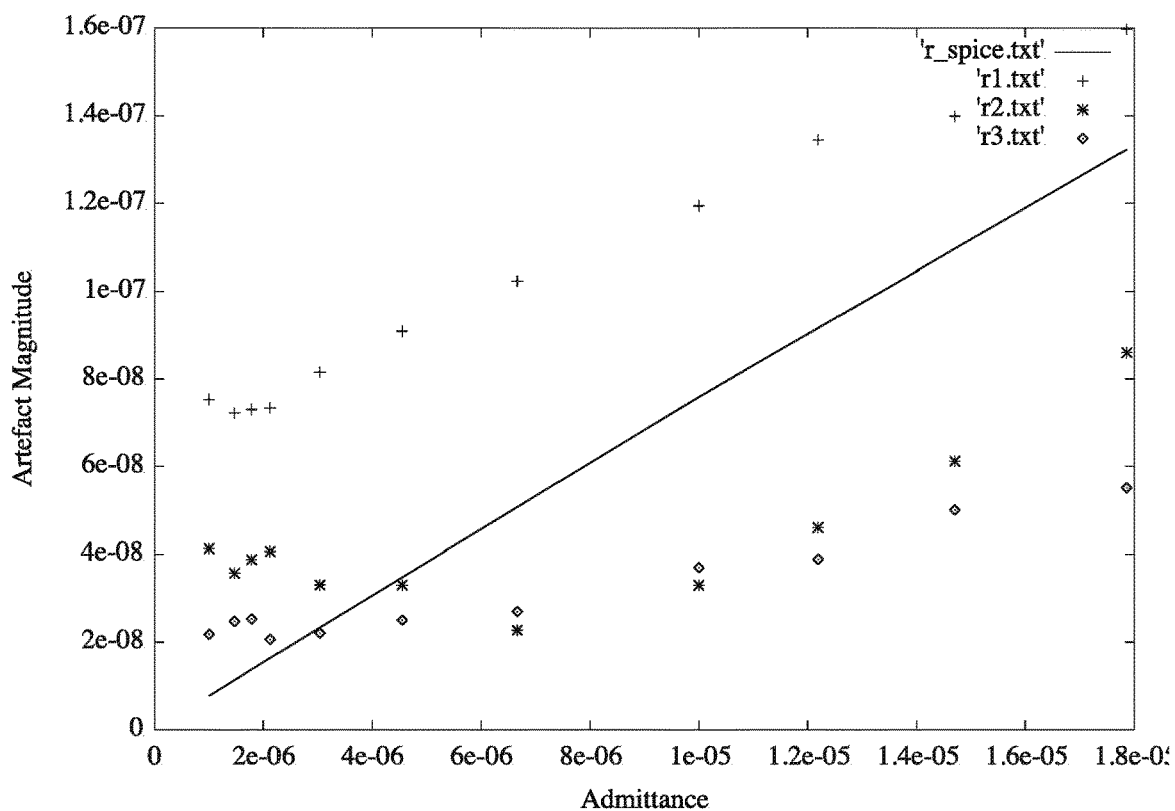
FIG. 10 shows artefact variation with resistance and capacitance.

FIG. 10 shows artefact variation when both resistance and capacitance are progressively changed.

Figure 11:
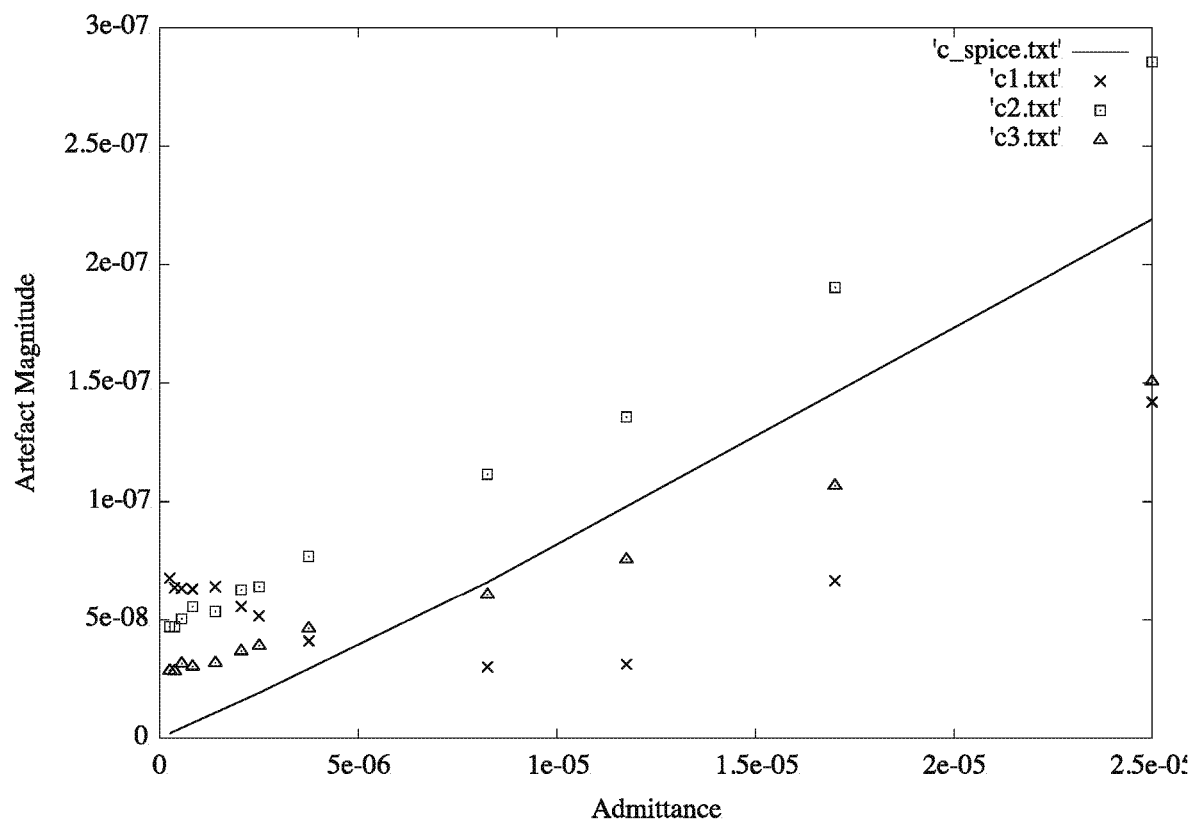
FIG. 11 shows RMS artefact variation with resistance and capacitance.

FIG. 11 shows artefact variation with resistance and capacitance using the above described RMS method.

In FIGS. 10 and 11, the curve dips then rises, consistent with FIG. 8. As expected, due to the DC offset, the RMS method obscures the fundamental accuracy of the model.

From the simulation model, using the above described baseline definition of artifact and a 400 us pulse width, the sensitivity of artefact to resistance is $4.1 \times 10^{-2}$V.s per mho, and the sensitivity of artefact to capacitance is $-2.85 \times 10^{-2}$ Vs per mho. Thus for a load of R, and where the artifact is over a 1 ms interval, then the voltage is $$V(r,t) = 4.1 \times 10^{-2}/(R \times t)$$

So for example, for an amplifier input resistance of 100 KΩ and a 1 ms artefact interval:

$$V(100k, 1ms) = 400uV$$

Further, for a capacitive load, and where the artifact is over a 1 ms interval, then the voltage is:

$$V(C,t) = -7.14 \times 10^{1} \times C/t$$

So for example for a 1000 pF load, artifact over 1 ms, artifact=71.4 uV.

Using this artefact calculation method, the following table shows the artifact contributions of various stray impedances which might be present in a typical SCS.

| Stray Impedance | Value | Artifact Contribution for 1 ms in uV |
|---|---|---|
| Cable | 350 p | 25 |
| input impedance | 50 k | 820 |
| Star load | 270 k | 152 |
| Output impedance of current source | 135 k | 304 |
| Reference inputs to amplifier | 83.3K | 492 |

As can be seen in the above table, appropriate adjustment and control of such impedances present in the neural measurement system can allow considerable sources of artefact to be reduced and ease the task measuring a neural signal of the order of 10 uV.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for measuring a neural response to a stimulus, the method comprising:
    applying an electrical stimulus from stimulus electrodes to neural tissue of a patient in order to evoke a neural response, wherein the electrical stimulus causes a differential voltage to arise on a sense electrode-tissue interface;
    amplifying a neural response signal sensed at two sense electrodes with a measurement amplifier to generate an amplified neural response signal;
    providing a respective sense electrode capacitor in series between each of the two sense electrodes and each of two respective inputs of the measurement amplifier,
    wherein the sense electrode capacitors are configured to have a capacitance that is greater than a threshold capacitance value, wherein the threshold capacitance value presents an impedance which ensures that a differential voltage arising across the sense electrode capacitors in response to the electrical stimulus is constrained to a level which permits differential measurement of the neural response signal sensed between the two sense electrodes; and measuring the amplified neural response signal.

2. The method of claim 1, wherein the measurement amplifier is configured to have an input impedance that is greater than a threshold impedance value, wherein the input impedance configuration of the measurement amplifier causes the differential voltage arising on the sense electrode-tissue interface to be constrained to a level which permits differential measurement of the neural response signal between the two sense electrodes, wherein the threshold impedance value is based on the differential voltage arising on the sense electrode-tissue interface in response to the electrical stimulus.

3. The method of claim 2 wherein the threshold impedance value is defined as:

$$A \times Z_C \frac{(V_{S1} - V_{S2})}{V_E}$$

where
- A is a scalar provided to give sufficient margin of $V_E$ over $(V_{S1} - V_{S2})$,
- $Z_C$ is a constant phase element impedance of each sense electrode,
- $V_{s1} - V_{s2}$ is the differential voltage arising on the sense electrode-tissue interface in response to the stimulus, and
- $V_E$ is a neural response voltage seen at the sense electrodes.

4. The method of claim 3 wherein A=1.

5. The method of claim 3 wherein A is greater than 0.067.

6. The method of claim 5 wherein A is greater than 0.5.

7. The method of claim 5 wherein A is greater than 1.

8. The method of claim 5 wherein A is greater than 2.

9. The method of claim 1 further comprising providing a respective stimulus electrode capacitor in series with each stimulus electrode.

10. The method of claim 9 wherein the stimulus electrode capacitors each have a respective capacitance which is the same as a capacitance of each sense electrode capacitor.

11. The method of claim 10 further comprising electrically reconfiguring at least one stimulus electrode as a sense electrode.

12. The method of claim 10 further comprising electrically reconfiguring at least one sense electrode as a stimulus electrode.

13. The method of claim 9 further comprising closing switches connecting the stimulus electrodes together, to equilibrate the stimulus electrodes prior to each stimulus.

14. The method of claim 13, wherein the switches are closed only in short bursts so that an equilibration current does not rise to a level which is perceivable by the patient.

15. The method of claim 1 wherein the sense electrode capacitors are chosen to have a respective capacitance of 5 pF.

16. The method of claim 1 further comprising obtaining neural measurements repeatedly over time and monitoring for changes in the neural response to a given stimulus.

17. The method of claim 16 further comprising providing feedback control of a therapy delivered to the patient.

18. An implantable device for measuring a neural response to a stimulus, the device comprising:
- a plurality of electrodes including one or more stimulus electrodes and two sense electrodes;
- a stimulus source for providing an electrical stimulus to be delivered from the one or more stimulus electrodes to neural tissue of a patient in order to evoke a neural response, wherein the electrical stimulus causes a differential voltage to arise on a sense electrode-tissue interface;
- a measurement amplifier for amplifying a neural response signal sensed at the two sense electrodes;
- a respective sense electrode capacitor in series between each of the two sense electrodes and each of two respective inputs of the measurement amplifier, the sense electrode capacitors each having a capacitance that is greater than a threshold capacitance value, wherein the threshold capacitance value presents an impedance which ensures that a differential voltage arising across the sense electrode capacitors in response to the electrical stimulus is constrained to a level which permits differential measurement of the neural response signal sensed between the two sense electrodes; and
- a control unit configured to control application of an electrical stimulus to the neural tissue and measurement of an evoked neural response, the control unit configured to apply an electrical stimulus from the stimulus electrodes to neural tissue, and the control unit further configured to amplify a neural response signal sensed at the sense electrodes with the measurement amplifier.

19. The device of claim 18, wherein the measurement amplifier is configured to have an input impedance that is greater than a threshold impedance value, wherein the input impedance configuration of the measurement amplifier causes the differential voltage arising on the sense electrode-tissue interface to be constrained to a level which permits differential measurement of the neural response signal between the two sense electrodes, wherein the threshold impedance value is based on the differential voltage arising on the sense electrode-tissue interface in response to the electrical stimulus.

20. The device of claim 19 wherein the threshold impedance value is defined as:

$$A \times Z_C \frac{(V_{S1} - V_{S2})}{V_R}$$

where
- A is a scalar provided to give sufficient margin of $V_E$ over $(V_{S1} - V_{S2})$,
- $Z_C$ is a constant phase element impedance of each sense electrode,
- $V_{s1} - V_{s2}$ is the differential voltage arising on the sense electrode-tissue interface in response to the stimulus, and
- $V_E$ is a neural response voltage seen at the sense electrodes.

21. The device of claim 20 wherein A=1.

22. The device of claim 20 wherein A is greater than 0.067.

23. The device of claim 22 wherein A is greater than 0.5.

24. The device of claim 22 wherein A is greater than 1.

25. The device of claim 22 wherein A is greater than 2.

26. The device of claim 18 further comprising a respective stimulus electrode capacitor in series with each stimulus electrode.

27. The device of claim 26 wherein the stimulus electrode capacitors each have a respective capacitance which is the same as a capacitance of each sense electrode capacitor.

28. The device of claim 27 wherein the control unit is further configured to electrically reconfigure at least one stimulus electrode as a sense electrode.

29. The device of claim 27 wherein the control unit is further configured to electrically reconfigure at least one sense electrode as a stimulus electrode.

30. The device of claim 26 further comprising switches connecting the stimulus electrodes together, and wherein the control unit is further configured to close the switches to equilibrate the stimulus electrodes prior to each stimulus.

31. The device of claim 30, wherein the control unit is further configured to close the switches only in short bursts so that an equilibration current does not rise to a level which is perceivable by the patient.

32. The device of claim 18 wherein the sense electrode capacitors are chosen to have a respective capacitance of 5 pF.

33. The device of claim 18 wherein the control unit is further configured to obtain neural measurements repeatedly over time and monitor for changes in the neural response to a given stimulus.

34. The device of claim 33 wherein the control unit is further configured to provide feedback control of a therapy delivered to the patient.

* * * * *